United States Patent [19]
Deighton

[11] Patent Number: 6,146,588
[45] Date of Patent: Nov. 14, 2000

[54] SHOE SANITIZER

[76] Inventor: Matthew L. Deighton, 2915 N. 42nd, Waco, Tex. 76710

[21] Appl. No.: 09/154,904

[22] Filed: Sep. 17, 1998

[51] Int. Cl.[7] .................................................. A01N 2/00
[52] U.S. Cl. ........................... 422/28; 422/292; 422/300; 15/104.92; 15/104.93; 15/215
[58] Field of Search ............... 422/28, 292, 300; 15/104.92, 104.93, 215

[56] References Cited

U.S. PATENT DOCUMENTS

| | | | |
|---|---|---|---|
| 2,602,724 | 7/1952 | Batchelor | 21/61 |
| 3,696,459 | 10/1972 | Kucera et al. | 15/104.92 |
| 3,911,520 | 10/1975 | Tupper | 15/104.92 |
| 4,425,677 | 1/1984 | Cox | 15/104.92 |
| 4,866,805 | 9/1989 | Oden et al. | 15/104.92 |
| 5,071,628 | 12/1991 | Alazet | 422/292 |
| 5,163,200 | 11/1992 | Carlin et al. | 15/104.92 |
| 5,164,164 | 11/1992 | Strickler et al. | 422/292 |
| 5,678,259 | 10/1997 | Cruz, Jr. | 4/622 |

*Primary Examiner*—David A. Redding
*Attorney, Agent, or Firm*—Howison, Chauza, Handley & Arnott LLP

[57] ABSTRACT

A shoe sanitizer and method for sanitizing shoes are disclosed. The shoe sanitizer includes a platform having a raised central portion and two lowered side portions which are on opposite sides of and adjacent to the central portion. The central portion and the two side portions have respective reservoirs with open upper ends. Absorbent pads are placed in each of the reservoirs. A sanitizing solution is placed in the reservoir of the central portion and saturates the respective absorbent pad. The absorbent pads located in the reservoirs of the side portions of the platform are dry. A person sanitizes the bottom of a pair of shoes he is wearing by first placing a lower portion of one shoe in the reservoir of the central portion and wetting the bottom of the shoe with the sanitizing solution. Then, the shoe is removed from the sanitizing solution and placed into the one of the reservoirs of the two side portions which corresponds to the foot on which the shoe being treated is worn. The bottom of the shoe is pressed against an absorbent pad to transfer the sanitizing solution from the shoe to the absorbent pad, drying the shoe. This process is repeated for the shoe being worn on the other foot of the user, utilizing the central reservoir to apply the sanitizing solution and the reservoir of the other of the two side portions to absorb the sanitizing solution and dry the second shoe.

20 Claims, 1 Drawing Sheet

SHOE SANITIZER

TECHNICAL FIELD OF THE INVENTION

The present invention relates in general to methods and utensils for cleaning and sterilizing items, and in particular to a method and apparatus for cleaning and sterilizing shoes to prevent the spread of bacteria and microorganisms which cause infectious diseases.

BACKGROUND OF THE INVENTION

Biocontamination presents a constantly increasing threat to human health. Bacteria and other microorganisms which cause infectious diseases are often spread by persons walking into contaminated areas and then carry the contaminants to other areas. For example, a person may walk through a contaminated area and his shoes may pick up bacteria or other microorganisms which may cause illness, and then the person may grab his shoes by the soles for removal from his feet. The contaminants are then spread from the soles of the shoes to the person's hands such that they may be ingested by that person or spread to a second person by touching either the second person or objects that the second person will also touch. This mode of transport can be especially troublesome in the food service and health care industries. The food service industry presents problems due to the large number of people that may be exposed to harmful bacteria and microorganisms by contaminated food and eating utensils. The health care industry poses special problems due to the high likelihood of encountering harmful bacteria and other microorganisms, such as the aids virus. In other circumstances, biocontaminants may be spread from the soles of contaminated shoes to household carpets, then small children and infants may crawl through a region of contaminated carpet and become infected with harmful bacteria and other microorganisms. Individuals may also contaminate household food and eating utensils by touching the soles of their shoes prior to using eating utensils. Contaminants are also be spread through mass transportation centers, such as airports, train stations, bus terminals and the like, transporting such bacteria and other microorganisms over potentially long distances. Harmful bacteria and other microorganisms have also been spread through oceangoing transportation and shipping facilities by passengers, seamen and stevadores walking through contaminants and then carrying the contaminants ashore on the bottoms of their shoes.

SUMMARY OF THE INVENTION

A shoe sanitizer and a method for sanitizing shoes are disclosed. The shoe sanitizer includes a platform having a central portion and two side portions. The two side portions are adjacent to and on opposite sides of the central portion of the platform. The central portion is at a higher elevation than the two side portions. The central portion and the two side portions each have reservoirs with open upper ends which are sized for receiving the bottom of a shoe to be sanitized. Absorbent pads are placed in each of the reservoirs. A sanitizing solution is placed in the reservoir of the central portion and saturates the absorbent pad. The absorbent pads which are located in the reservoirs of the side portions of the platform are initially dry. A person sanitizes the bottom of a pair of shoes he is wearing by first placing a lower portion of one shoe in the reservoir of the central portion and wetting the bottom of the shoe with the sanitizing solution. Then, the shoe is removed from the sanitizing solution and the reservoir of the central portion, and placed into the one of the reservoirs of the two side portions which corresponds to the foot on which the shoe being treated is worn. The bottom of the shoe is pressed against the corresponding absorbent pad to transfer the sanitizing solution from the shoe to the absorbent pad, drying the shoe. This process is repeated for a second shoe which is preferably being worn on the other foot of the user, utilizing the central reservoir to apply the sanitizing solution and the absorbent pad located in the reservoir of the other of the two side portions to absorb the sanitizing solution to dry the second shoe.

BRIEF DESCRIPTION OF THE DRAWINGS

For a more complete understanding of the present invention and the advantages thereof, reference is now made to the following description taken in conjunction with the accompanying Drawings in which.

DETAILED DESCRIPTION OF THE INVENTION

Figure 1:
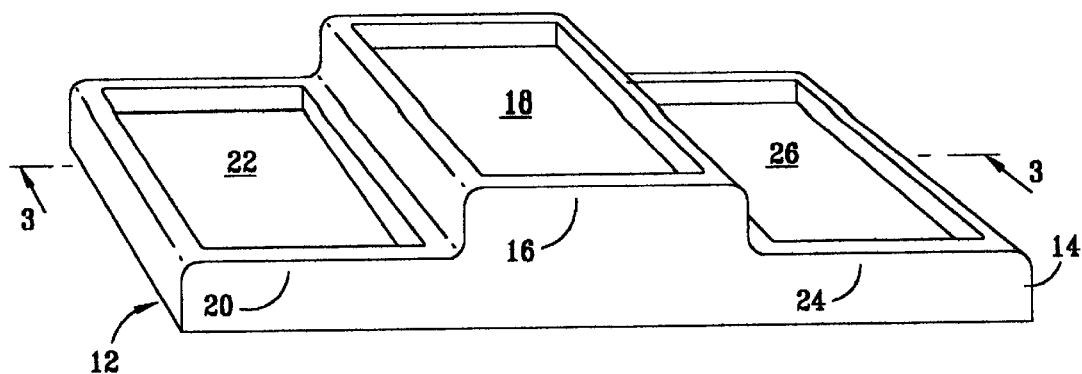
FIG. 1 is perspective view of a shoe sanitizer.

FIG. 1 is a perspective view of a shoe sanitizer 12 made according to the present invention. The shoe sanitizer 12 has a platform 14 which includes a central portion 16. The central portion 16 has a first reservoir 18. The platform 14 further includes a side portion 20 having a second reservoir 22, and a side portion 24 having a third reservoir 26. The central portion 16 is located at an elevation which is higher than the two side portions 20 and 24. The two side portions 20 and 24 are adjacent to and on opposite sides of the central portion 16, and disposed at a lower elevation than that of the central portion 16. Preferably, the platform 14 is formed as a singular member of molded plastic.

Figure 2:
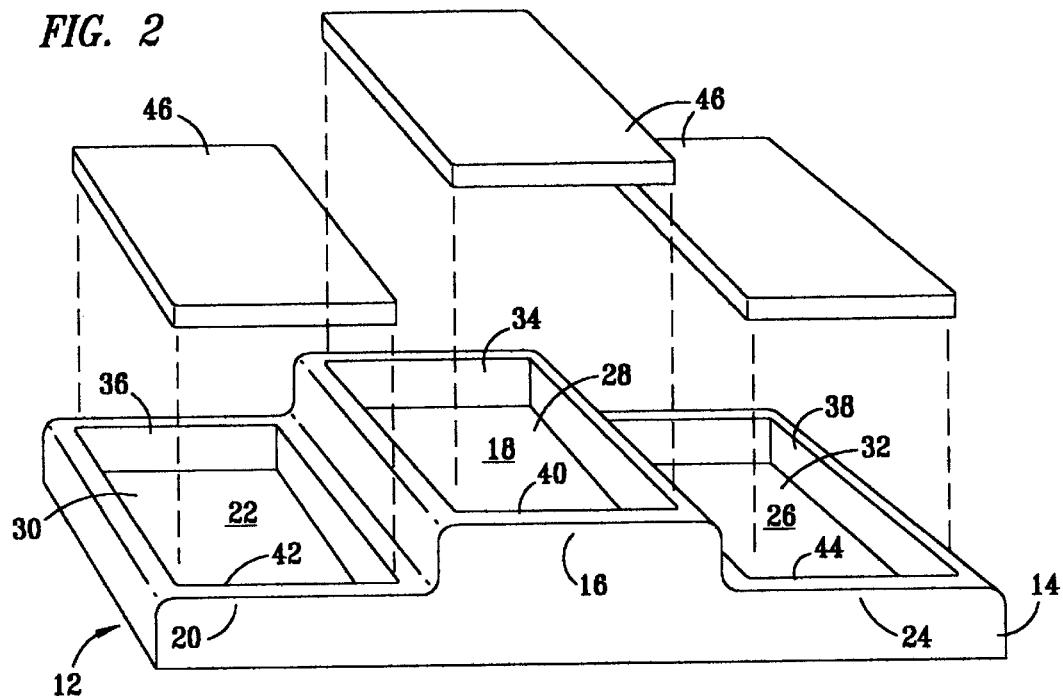
FIG. 2 is an exploded view, shown in perspective, of the shoe sanitizer.

FIG. 2 is an exploded view of the shoe sanitizer 12, depicted in perspective. The reservoirs 18, 22 and 26 have lower ends 28, 30 and 32, respectively, sidewalls 34, 36 and 38, respectively, and upper ends 40, 42 and 44, respectively. The lower ends 28, 30 and 32 are closed and sealed at respective ones of the adjacent sidewalls 34, 36 and 38. The upper ends 40, 42 and 44 of respective ones of the reservoirs 18, 22 and 26 are open and sized such that they may receive the lower portion of standard sized shoes, at least one at a time. In the preferred embodiment, the tops of the central portion 16 and each of the two side portions 20 and 24 measure 8 inches by 15 inches. The reservoirs 18, 22 and 26 are spaced apart from respective ones of the outer edge of the platform 14 by approximately one-eighth inches to one-quarter inches. The tops of the upper ends 42 and 44 are spaced above the bottom of the platform 14 approximately two inches. The upper end 40 of the first reservoir 18 is approximately three inches taller than the upper ends 42 and 44 of the second and third reservoirs 22 and 26, respectively. Three absorbent pads 46 are placed in the platform 14, with one of the pads 46 being placed in each of the reservoirs 18, 22 and 26. The absorbent pads 46 are preferably formed of a cellulose sponge cloth which is approximately one-eighth inches thick, when dry, to three-sixteenth inches thick when wet.

Figure 3:
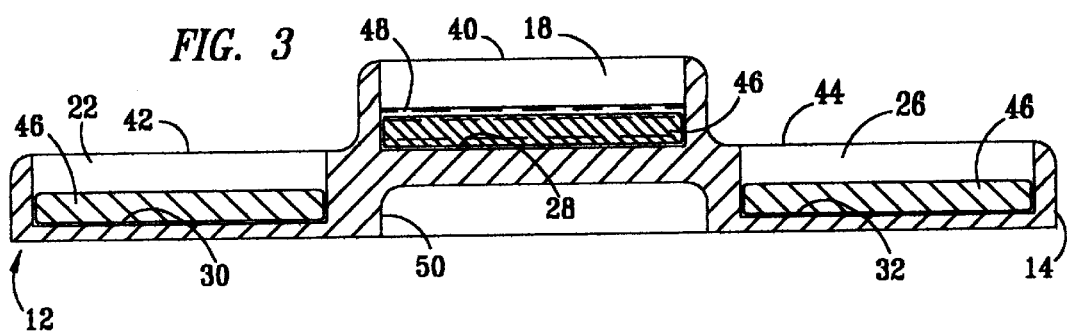
FIG. 3 is sectional view of the shoe sanitizer, taken along section line 3—3 of FIG. 1.

FIG. 3 is a sectional view of the shoe sanitizer 12, taken along a vertical sectioning plane defined by section line 3—3 of FIG. 1. The platform 14 has an open lower cavity 50, with the opening of the lower cavity 50 facing downward. The height of the open end 40 of the reservoir 18 is disposed above the open ends 42 and 44 of the respective one of the reservoirs 22 and 26. Preferably, the lower end 28 of the reservoir 40 is aligned to be substantially at the same elevation as the upper ends 42 and 44 of respective ones of the reservoirs 22 and 26. A sanitizing solution 48 is disposed within the first reservoir 18, saturating the absorbent pad 46 which is placed in the first reservoir 18 and filling the reservoir 18 to a level which is slightly above the height of the top of the respective absorbent pad 46. Preferably, the sanitizing solution is provided by a liquid, non-acid, foaming cleaner, disinfectant, deodorizer and mildewstat sold under the trade name PATH-O-CIDE, which is manufactured by Imperial Industries of Texas, Inc., in Dallas, Tex. It is of the chemical family Quatemary Ammonium Cleaner Disinfectant, and is effective as a disinfectant agent against *Mycobacterium tuberculosis, Staphylococcus aureus, Salmonella choleraesuis, Pseudomonas aeruginosa, Trichophyton interdigitale* (Athletes foot fungus), and HIV-1 (Aids virus).

In operation, the shoe sanitizer 12 is utilized by a user to clean a pair of shoes which are being worn by the user. The platform 14 of the shoe sanitizer 12 is placed upon a ground surface close to an entry into a region to be sanitized, such as a food service kitchen, a hospital ward, a household or an entrance into a mass transit facility, or an exit from such a mass transit facility, a shipping facility, an ocean going vessel or an airplane. The absorbent pads 46 arc placed in respective ones of the reservoirs 18, 22 and 26. The sanitizing solution 48 is placed into the first reservoir 18, saturating the respective absorbent pad 46, and preferably providing a thin layer of the sanitizing solution 48 which is disposed atop the absorbent pad 46. A user approaches the shoe sanitizing station 12, and then places one the shoes he is wearing within the first reservoir 18 of the central portion 16 by picking up his foot to an elevation which is above the upper opening 40 of the first reservoir 18, and then lightly stepping into the first reservoir 18 until the sanitizing solution 48 wets to the bottom of the shoe being treated. The central portion 16 is raised above the adjacent side portions 20 and 24 such that the one of the reservoirs 18, 22 and 26 in which the sanitizing solution 48 is disposed for application to the bottom of shoes is clearly identified.

The raised central portion 16 requires that a user raise his foot to step slightly upward and above the side portions 20 and 24 to step into the reservoir 18 for application of the sanitizing solution to the bottom of a shoe. Then, the user will remove the shoe from the first reservoir 18, and place the lower portion of the shoe into the respective one of the reservoirs 22 and 26 which, with respect to the user, corresponds to whether the shoe being sanitized is on the right of left foot of the user. The user will then press the bottom of the shoe being treated against the absorbent pad 46 which is in the corresponding one of the reservoirs 22 and 26 to transfer the sanitizing solution 48 from the bottom of the shoe being treated to the absorbent pad 46 in the corresponding one of the reservoirs 22 and 26 to dry the sanitizing solution 48 from the shoe. The process is then repeated for the other shoe, by first placing the lower portion of the shoe within the reservoir 18 until it is wetted with sanitizing solution 48, removing the shoe from the first reservoir 18, and then placing the shoe within the one of the reservoirs 22 and 26 which is located on a side of the central portion 16 which corresponds to whether the second foot upon which the shoe is disposed that is being cleaned is the right foot or the left foot of the user. The shoe is then pressed against the absorbent pad 46 which is located in the other of the reservoirs 22 and 26 to transfer the sanitizing solution 48 from the shoe to the absorbent pad 46.

The shoe sanitizer of the present invention provides several advantages. A shoe sanitizer is provided for use to treat the bottom of shoes to prevent the spread of bacteria and other microorganisms which may cause infectious diseases. The shoes are preferably treated while being worn by lightly stepping into the shoe sanitizer and pressing the bottom of the shoes against absorbent pads. The shoe sanitizer has a raised central portion which provides a person with a visual indication of which reservoir contains the sanitizing solution. Adjacent side portions are provided for a person to then step upon to remove the sanitizing solution from the bottom of the shoes after being treated with the sanitizing solution. The raised central portion also provides that a person sanitizing shoes must step slightly upwards such that the lower portion of the shoes may be more clearly seen as the sanitizing solution is being applied to the bottom of the shoe. The improved visibility provided by the step may also prevent a person from misstepping, which could cause injury. The reservoirs provide containment facilities to prevent the sanitizing solution from spilling upon the floor.

Although the preferred embodiment has been described in detail, it should be understood that various changes, substitutions and alterations can be made therein without departing from the spirit and scope of the invention as defined by the appended claims.

What is claimed is:

1. An apparatus for sanitizing shoes, comprising:

a platform having a central portion and two side portions, said central portion being disposed between and adjacent to said two side portions;

said central portion having a first reservoir which includes an open upper end which is sized for receiving at least lower portions of the shoes and a sanitizing solution for application to the lower portions of the shoes;

said two side portions of said platform having a second reservoir and a third reservoir, respectively, and said second and third reservoirs each having upwardly disposed openings which are sized for receiving the shoes;

a plurality of absorbent pads, with respective ones of said absorbent pads disposed in each of said first, second and third reservoirs, a first one of said absorbent pads being disposed in said first reservoir for saturating with said sanitizing solution and engaging with the lower portions of the shoes for application of said sanitizing solution to the lower portions of the shoes, and second and third ones of said absorbent pads being disposed in said second and third reservoirs, respectively, for engaging with the lower portion of the shoes for removal of said sanitizing solution from said shoes; and said sanitizing solution being disposed in said first reservoir of said central portion and saturating said first one of said absorbent pads.

2. The apparatus of claim 1, wherein at least one of said central portion and said two side portions is disposed at an elevation above elevations of at least one of the others of said central portion and said two side portions.

3. The apparatus of claim 1, wherein said second and third reservoirs each include lower ends which are substantially co-planar.

4. The apparatus of claim 1, wherein said first, second and third reservoirs have sealed lower ends and sealed sidewalls.

5. The apparatus of claim 1, wherein said first, second and third reservoirs have substantially planar horizontal lower surfaces and substantially planar vertical sidewalls, and said reservoirs have rectangular cross sections in at least one cross-sectioning plane.

6. The apparatus of claim 1, wherein said first, second and third reservoirs have substantially planar horizontal lower surfaces and substantially planar vertical sidewalls, and said reservoirs have rectangular cross sections in at least two cross-sectioning planes which are mutually perpendicular.

7. The apparatus of claim 1, wherein at least one of said central portion and said two side portions is disposed at an elevation above elevations of the other of said central portion and said two side portions; and wherein said second and third reservoirs each include lower ends which are substantially co-planar.

8. The apparatus of claim 7, wherein said first, second and third reservoirs have sealed lower ends and sealed sidewalls.

9. The apparatus of claim 7, wherein said first, second and third reservoirs have substantially planar horizontal surfaces and substantially planar vertical sidewalls, and said reservoirs have rectangular cross sections in at least one cross-sectioning plane.

10. The apparatus of claim 8, wherein said first, second and third reservoirs have substantially planar horizontal surfaces and substantially planar vertical sidewalls, and said reservoirs have rectangular cross sections in at least two cross-sectioning planes which are mutually perpendicular.

11. An apparatus for sanitizing shoes, comprising:

a platform having a raised central portion and an adjacent side portion, said raised central portion being disposed at an elevation which is above said adjacent side portion;

said raised central portion having a first reservoir which includes a first reservoir open upper end which is sized for receiving at least lower portions of the shoes and a sanitizing solution for application to the lower portions of the shoes;

said adjacent side portion of said platform being disposed adjacent to said raised central portion, and having a second reservoir with an upwardly disposed opening which is sized for receiving the shoes;

a plurality of absorbent pads, with respective ones of said absorbent pads disposed in each of said first and second reservoirs, a first one of said absorbent pads being disposed in said first reservoir for saturating with said sanitizing solution and engaging with the lower portions of the shoes for application of said sanitizing solution to the lower portions of the shoes, and a second one of said absorbent pads being disposed in said second reservoir for engaging with the lower portion of the shoes for removal of said sanitizing solution from said shoes; and said sanitizing solution being disposed in said first reservoir of said central portion and saturating said first one of said absorbent pads.

12. The apparatus of claim 11, further comprising a third side portion having third reservoir, disposed adjacent to said raised central portion, wherein said second and third reservoirs each include lower ends which are substantially co-planar.

13. The apparatus of claim 11, further comprising a third side portion having a third reservoir disposed adjacent to said first reservoir, and wherein said first, second and third reservoirs have sealed lower ends and sealed sidewalls.

14. The apparatus of claim 11, further comprising a third side portion having a third reservoir disposed adjacent to said raised central portion and on an opposite side of said raised central portion from said first portion, wherein said first, second and third reservoirs have substantially planar horizontal surfaces and substantially planar vertical sidewalls, and said reservoirs have rectangular cross sections in at least one cross-sectioning plane.

15. The apparatus of claim 14, wherein said first, second and third reservoirs have sealed lower ends and sealed sidewalls.

16. The apparatus of claim 11, wherein said first and second reservoirs have substantially planar horizontal surfaces and substantially planar vertical sidewalls, and said reservoirs have rectangular cross sections in at least two cross-sectioning planes which are mutually perpendicular.

17. The apparatus of claim 16, wherein said first and second reservoirs have sealed lower ends and sealed sidewalls.

18. A method for sanitizing a shoe, comprising the steps of:

providing a platform having a central portion and an adjacent side portion, the adjacent side portion being disposed adjacent to the central portion, the central portion and the adjacent side portion having first and second reservoirs, respectively, wherein the first and second reservoirs have respective first and second absorbent pads, and have first and second open upper ends which are sized for receiving at least a lower portion of the shoe, wherein the first and second open upper ends are spaced apart at first and second elevations, respectively;

placing a sanitizing solution onto a first one of the absorbent pads which is disposed within the first reservoir, and wetting the first one of the absorbent pads with the sanitizing solution;

placing the lower portion of the shoe through the open upper end of the first reservoir and disposing the lower portion at the first elevation, such that the lower portion of the shoe is pressed against the first absorbent pad and wetted with the sanitizing solution;

removing the lower portion of the shoe from within the first reservoir, and then disposing the lower portion of the shoe at the second elevation within the second reservoir, wherein the second elevation is spaced apart from the first elevation;

pressing the lower portion of the shoe against the second absorbent pad to transfer the sanitizing solution from the lower portion of the shoe to the second absorbent pad; and then, removing the lower portion of the shoes from within the second reservoir.

19. The method of claim 18, wherein the step placing the lower portion of the shoe through the open upper end of the first reservoir and disposing the lower portion at the first elevation disposes the lower portion at a higher elevation than the step of placing the lower portion of the shoe at the second elevation in the second reservoir.

20. The method of claim 18, further comprising the steps of:

providing a third reservoir which is adjacent to the first reservoir and on an opposite side of the first reservoir from the second reservoir, said third reservoir having an upwardly disposed open upper end and a third absorbent pad disposed therein;

placing the lower portion of a second shoe, which is worn on an opposite foot of the user than that of the above shoe, through the open upper end of the first reservoir and disposing the lower portion of the second shoe at the first elevation, such that the lower portion of the second shoe is pressed against the first absorbent pad and wetted with the sanitizing solution;

removing the lower portion of the second shoe from within the first reservoir, and then disposing the lower portion of the second shoe at substantially the second elevation within the third reservoir; and pressing the lower portion of the second shoe against the third absorbent pad for removal of the sanitizing solution from the second shoe.

\* \* \* \* \*